Figure 1:
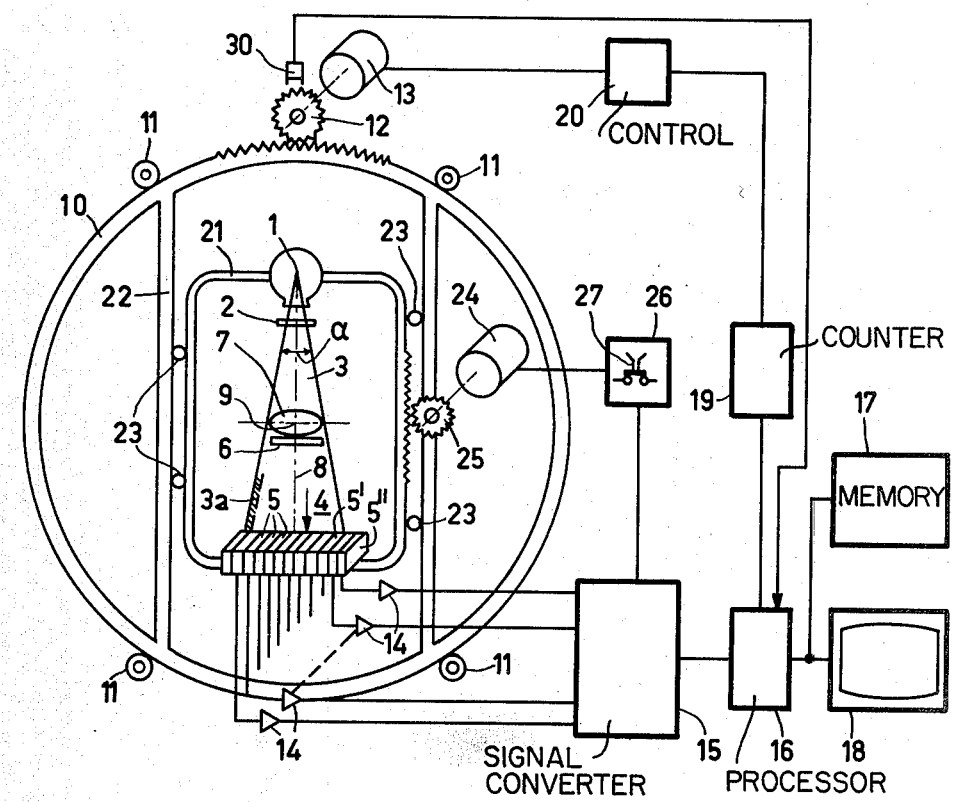

United States Patent [19]

Lux

[11] 4,374,419
[45] Feb. 15, 1983

[54] DEVICE FOR DETERMINING A RADIATION ATTENUATION DISTRIBUTION IN A PLANE OF A BODY

[75] Inventor: Peter W. Lux, Friedrichshafen, Fed. Rep. of Germany

[73] Assignee: U.S. Philips Corporation, New York, N.Y.

[21] Appl. No.: 166,887

[22] Filed: Jul. 8, 1980

[30] Foreign Application Priority Data

Jul. 6, 1979 [NL] Netherlands ............... 7905282

[51] Int. Cl.³ .............................................. A61B 6/00
[52] U.S. Cl. ..................................... 364/414; 378/901
[58] Field of Search .................... 250/445 T; 364/414

[56] References Cited

U.S. PATENT DOCUMENTS 4,135,247 1/1979 Gordon et al. ................. 250/445 T

OTHER PUBLICATIONS

Alvarez, R. E., *Extraction of Energy Dependent Information*, (Doctoral Dissertation) Jul. 1976, pp. 100–102.

Primary Examiner—Alfred E. Smith
Assistant Examiner—T. N. Grigsby
Attorney, Agent, or Firm—Jack E. Haken

[57] ABSTRACT

For the backprojection of the convoluted measurement signals in a cartesian coordinate system in a computer tomography device, it is necessary to recalculate the weighting factors for each position of the source in order to determine the contribution of a convoluted measurement signal to the attenuation value associated with a given element of the output image matrix. This is a time consuming and hence expensive form of reconstruction, and can be avoided by storing all the weighting factors required; this, however, implies a very large memory, and is also expensive.

The invention relates to the use of a matrix of elements organised in polar coordinates, which is stored in the memory, the origin central coordinate of said matrix coinciding with the center of rotation of the X-ray source about the object section. The weighting factors are also stored in a polar organized memory. The angular component of the address of the weighting factors is incremented with a rotational increment in the corresponding position of the X-ray source, so that for each group of measurement values, the same weighting factors can be used. The invention enables all the weighting factors to be stored in a memory of limited capacity, the more so because all weighting factors are mirror-symmetrical with respect to a central axis connecting the X-ray source to the center of rotation, so that the angular coordinates of the memory need only extend from 0 to $\pi$ instead of from 0 to $2\pi$.

3 Claims, 4 Drawing Figures

DEVICE FOR DETERMINING A RADIATION ATTENUATION DISTRIBUTION IN A PLANE OF A BODY

The invention relates to a method of determining the radiation attenuation distribution in a sectional plane of a body, the sectional plane being successively irradiated in a plurality of directions at equal angular increments by means of a flat, fan-shaped beam of radiation which is directed in the sectional plane and which penetrates and spans the body section, radiation having passed through the body being detected in order to generate groups of measurement signals which represent the attenuation of radiation in the body along corresponding groups of measurement paths, each group of measurement paths extending from a common point of origin in a fan-shaped manner so as to subdivide the fan-shaped beam of radiation after which, in order to determine the radiation attenuation distribution, each group of measurement signals is consecutively convoluted with a series of numbers so as to obtain a group of convolved values, the group of convolved values being back projected onto a matrix of elements along paths which are determined by the associated group of measurement paths, a fixed relationship existing between the matrix of elements and the body section, a contribution to an attenuation value associated with an element being determined by the product of a convolved value associated with the measurement path extending through the element and a weighting factor which is inversely proportional to the square of the distance between the element and the common point of origin of the measurement paths, the attenuation distribution being formed by building up the attenuation values associated with each respective element by summing the contributions relating to that element.

The invention furthermore relates to a device for determining the radiation attenuation distribution in a sectional plane of a body, said device comprising: a radiation source for generating a flat, fan-shaped beam of radiation which is directed in the sectional plane and which penetrates and spans the body section, a detector device for detecting radiation after passing through the body and for supplying groups of measurement signals, a supporting frame for supporting the radiation source and the detector device, drive means for moving at least the radiation source in the supporting frame in order to irradiate the body from a plurality of directions, the detector device supplying a group of measurement signals for each direction which respectively represent the radiation attenuation along each of a group of measurement paths which extend fan-wise from the radiation source, a processing device for convoluting a group of measurement signals with a series of numbers and for backprojecting the measurement signals thus convoluted in order to obtain attenuation values, a memory device for storing the attenuation values, and a display device for displaying the attenuation values associated with the elements of a matrix in which the radiation attenuation distribution is imaged.

A method and a device of this kind are described in Netherlands Patent Specification No. 7614230 laid open to public inspection. Said Application clearly describes how the measurement signals required for the reconstruction of an attenuation distribution, are measured by means of a fan-shaped beam of X-rays and an array of detectors which supplies a group of measurement signals for each position of the X-ray source. The series of numbers with which each of these groups of measurement signals is to be convoluted for the calculation of the groups of convolved values is also derived in said Application. It is also stated that an attenuation value at a given point is determined by summing the convolved values associated with paths which extend through this point, each convolved value being multiplied, prior to summing, by a weighting factor which is inversely proportional to the square of the distance between the point and the position of the X-ray source associated with the convolved value. The described method of backprojection is a complex and time consuming and hence unattractive operation.

The invention has for its object to provide a method and a device whereby and wherein backprojection is performed in a comparatively simple manner.

To achieve this, the method in accordance with the invention is characterized in that the matrix of elements is a polar matrix in which an element is addressed by a distance coordinate from a central origin and an angular coordinate about said origin, corresponding weighting factors for a given group of measurement signals being stored in a further polar matrix which is addressed by the same distance coordinate and the same angular coordinate, the corresponding respective said addresses formed by said angular coordinates being caused to differ by one or a further respective increment after each operation comprising convolution of a said group of measurement signals and back-projection of the corresponding group of convolved values, said increment being equal to the angular increment between the directions associated with the groups to be successively processed.

A method of this kind offers the advantage that the same weighting factors can be used for the backprojection of each group of convolved values. The geometry of the backprojection does not change with respect to the geometry of the elements of the reconstruction matrix, except for the angular rotation of the radiation source between the measurement of two groups of measurement signals or convolved values. Because use is made of a second matrix in which the weighting factors are stored and which is also addressed according to polar coordinates, the weighting factors can be fetched by using the same addressing procedure as for previously calculated contribution after shifting the weighting factors in the second matrix addresswise through an angle relative to the element matrix which equals the angle of rotaton of the X-ray source. After multiplication of the weighting factors, and the convolved value the contribution is added to a value stored at the given address. The addresswise rotation of the weighting factors in the second matrix actually consists only of a fixed increment in the angular coordinate in the address of a weighting factor with respect to the angular coordinate in the address of the location to which the contribution to be calculated is assigned.

A device in accordance with the invention is characterized in that the memory device comprises a first memory arranged to be addressed using polar coordinates in which the attenuation values are to be stored by addressing with a distance coordinate and an angular coordinate, and a second memory with similar form of polar address organization in which weighting factors are stored for use during backprojection of the convolved values. A device of this kind offers the advantage that, by contrast with a device comprising a memory in which the elements are addressed with carthesian coordinates, the storage space for the weighting factors is comparatively small and hence inexpensive. This is because when use is made of a memory with carthesian coordinates, a separate set of weighting factors must be used for each source position (other irradiation direction through the body and actually through the matrix); said separate set can be calculated in advance, but an enormous and hence expensive, storage space is then required.

The method and device in accordance with the invention will be described hereinafter with reference to the accompanying diagrammatic drawing.

Figure 2:
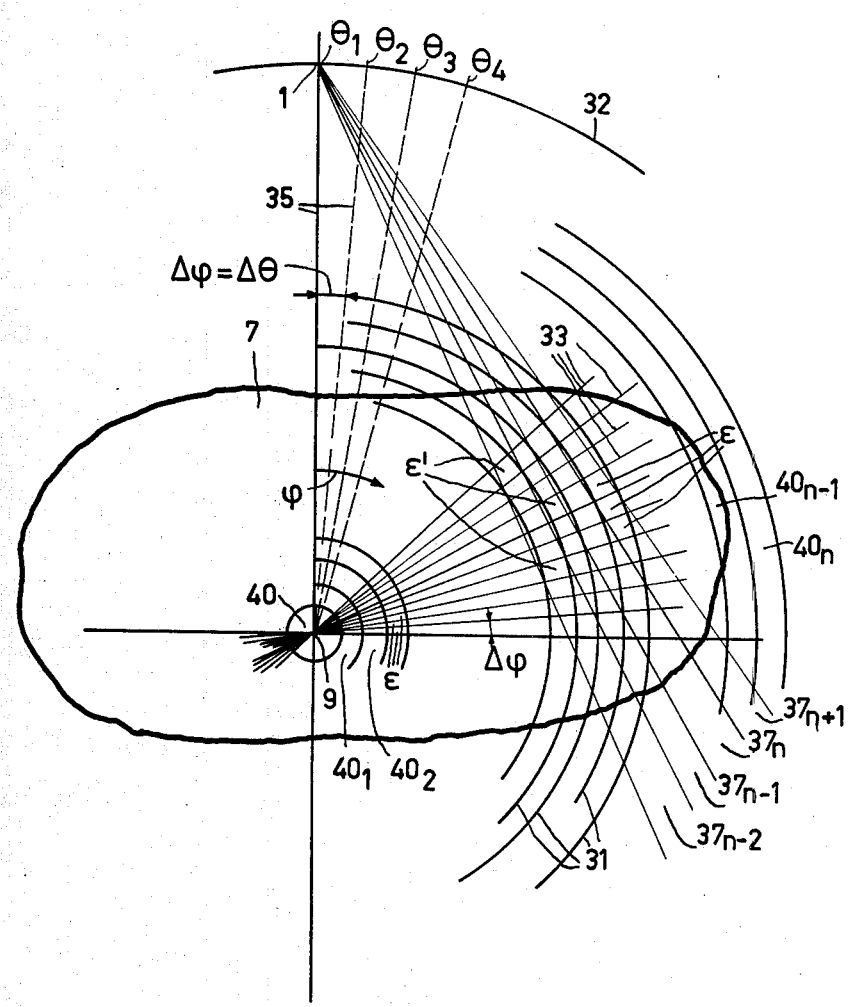
Figure 3:
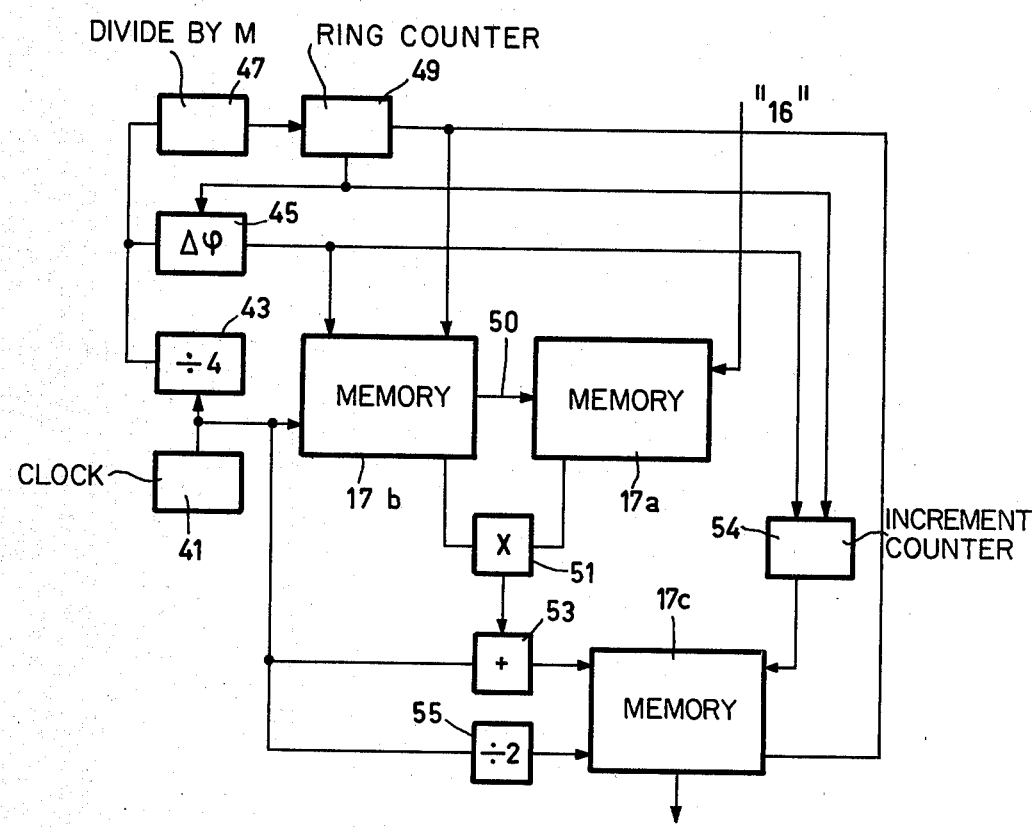
Figure 4:
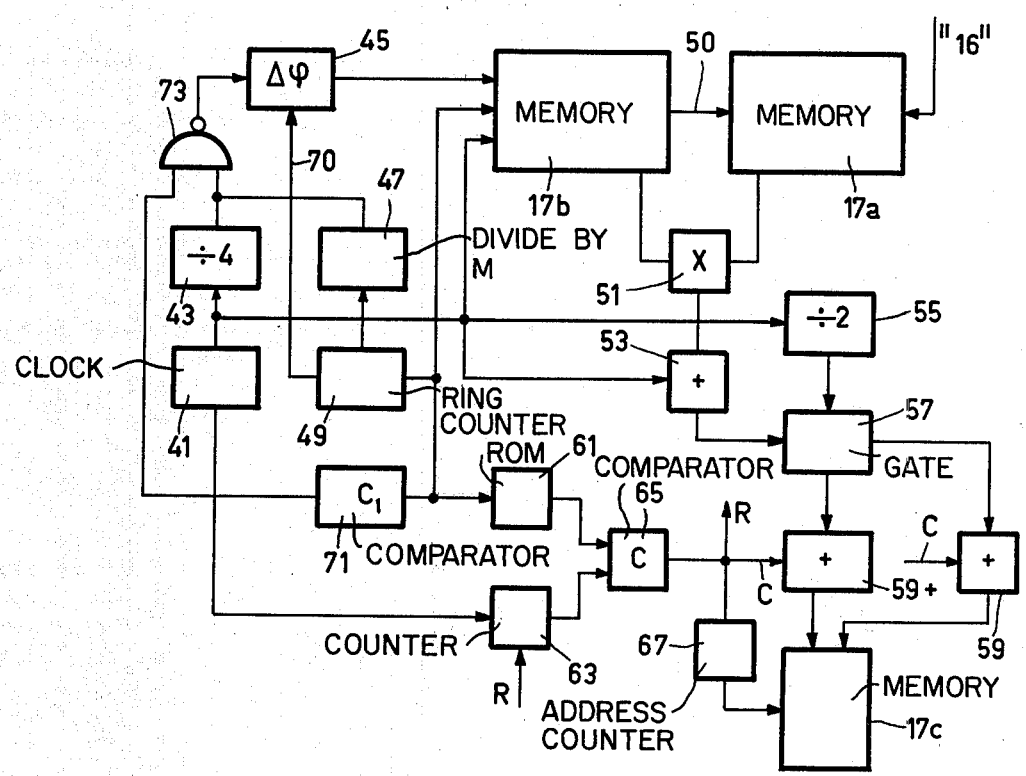

FIG. 1 shows a computer tomography device in accordance with the invention,

FIG. 2 shows a matrix of elements in order to illustrate the determination of contributions of absorption values in accordance with the invention, FIG. 3 shows a block diagram of an embodiment of a processing device and a memory device for the computer tomography device shown in FIG. 1, and FIG. 4 shows a block diagram of a preferred embodiment of a part of a processing device and a memory device for the computer tomography device shown in FIG. 1.

The computer tomography device which is diagrammatically shown in FIG. 1 comprises a radiation source 1 which is preferably an X-ray source but which may alternatively consist of a radioactive isotope, for example, Am 241. Using a diaphragm 2, the radiation emitted by the radiation source 1 is limited to form a diverging radiation beam 3 which is situated in a plane, the thickness of the radiation beam 3 in a direction perpendicular to the plane being, for example, from 3 to 25 mm, its divergence in the plane being determined by the angle $\alpha$. The radiation beam 3 is incident on a detector array 4 which comprises individual detectors 5 which measure the radiation and which define radiation beams 3a, the width and the spacing distance of the individual detectors 5 with respect to each other determining the spacial accuracy with which an object arranged on an object table 6 is scanned. A detector array 4, which is symmetrically positioned with respect to a central ray 8, can comprise for example 300 detectors 5, the centre-to-centre distance between two detectors 5 being a few millimeters. The detector array can alternatively be an elongate, gas-filled ionization chamber in which electrodes which detect ionization in separate zones, are arranged in a row. The object 7 is slidable perpendicularly to the plane of the radiation beam 3 in the longitudinal direction of an axis 9 which is situated within the object 7 and which represents the central axis of the circular supporting frame 10, so that different sectional layers of the object 7 can be irradiated.

The system formed by the radiation source 1 and the detector array 4 is arranged to be rotatable about the axis 9, so that a sectional layer of the object 7 can be irradiated by the radiation beam 3 in different directions which are situated within the layer. The rotation of the supporting frame 10, which is journalled by means of bearings 11, is realized by drive means such as a gearwheel 12 and a motor 13. The rotation of the supporting frame 10 may be continuous or intermittent, the object 7 being irradiated by flashing the radiation source 1 after each step, in the latter case.

The measurement signals from the detectors 5 are amplified by means of an amplifier 14 and are applied to a signal converter 15 in which the measurement signals are corrected in known manner for "offset", related to a reference value, digitized, logarithmically converted, and calibrated on the basis of the logarithmic conversion and calibration tables incorporated in the signal converter. Digital measurement values are applied from the output of the converter 15 to a processing device 16. The digitized measurement values are converted, by means of the processing device 16, into attenuation values which represent a reconstruction image and which are stored in a memory device 17. The calculated attenuation values can be displayed on a display device, for example, a monitor 18. A counter 19 counts the number of measurement signals applied to the processing device 16 per group of measurement signals. As soon as the number of measurement signals corresponds to the number of detectors 5, a control circuit 20 is activated which briefly activates the motor 13, thus realizing a rotation of the supporting frame 10. Subsequently, the next group of measurement signals is measured, etc. Using an optical sensor 30, the angular rotation $\theta$ between the successive measurement series is determined by counting the teeth of the gearwheel 12. The pulses generated by the sensor 30 are applied to the processing device 16 so that, in conjunction with the data laid down in the processing device concerning the geometric construction of the supporting frame 10, and the relative disposition of the source 1 and the detector device 4, the coordinates relating to all the measurement paths associated with each group of measurement signals, can be determined.

It has been found that the distance between the radiation source 1 and the object 7 should preferably be adaptable to the diameter of the object 7. To achieve this, the system formed by the radiation source 1 and the detector array 4 is mounted on a support 21 which can be displaced along guide rails 22 on bearings 23 by means of a gearwheel drive 25 which is coupled to a motor 24. A control circuit 26 can be operated, for example, by means of a manual switch 27; however, automatic operation of the circuit 26 is also possible. Prior to the start of the measurement, the measurement signals from two detectors 5' and 5" are applied to the control circuit 26 via the signal converter 15. The support 21 is displaced so that the measurement signal from the detector 5" becomes a maximum, whilst the measurement signal from the detector 5' has a slightly lower value. The detector 5" then receives radiation which has not passed through the object 7, but only through the space surrounding the object 7, while the radiation measured by the detector 5' has been attenuated by the object 7. Subsequently, the control circuit 26 is locked in order to keep the distance between the radiation source 1 and the axis of rotation 9 constant during the exposure.

The method and the computer tomography device in accordance with the invention will be described in detail with reference to FIG. 2. During the measurement procedure, the source 1 successively occupies the positions $\theta_1$, $\theta_2$, $\theta_3$, etc. on a circular path 32 having a centre 9, the body 7 and the matrix comprising the elements $\epsilon$ which is permanently associated therewith remaining stationary. The boundaries of the respective elements $\epsilon$ of the matrix are defined by corresponding portions of concentric circles 31 and of radial lines 33 which pass through the centre 9, only part thereof being shown. The angle $\Delta\phi$ which is enclosed by an adjacent pair of radial lines 33, equals the angle $\Delta\phi$ enclosed by two neighbouring connecting lines between the source positions $\theta_1$, $\theta_2$ and the centre 9. From a group of measurement signals, determined with the source in the position $\theta_1$ along a group of measurement paths (only a part thereof is shown in the Figure), convolved values are determined in known manner; these convolved values have to be backprojected onto the respective elements $\epsilon$ along the measurement paths $37_{n-1}$, $37_n$, $37_{n+1}$, ... in order to determine the corresponding contribution to be made to the attenuation value represented by each element $\epsilon$. To achieve this, the convolved value is weighted by multiplication by a weighting factor which is, for example, proportional to the area which is common to the element $\epsilon$ and the associated measurement path 37, and is inversely proportional to the square of the distance R between the source 1 and the relevant element $\epsilon$. The weighting factors are stored in a matrix store having the same organizational arrangement as the matrix store containing the elements $\epsilon$ for storing and reproducing the computed radiation absorption distribution. In each memory location of the matrix there are stored two (one) weighting factors with which a convolved value associated with a measurement path, extending through the element $\epsilon$ is multiplied. The memory location also contains, in addition to the weighting factor(s), the measurement path number (numbers) ( .. . n-1, n, n+1, n+2 ... ) which indicate the measurement path $37_{n-1}$, $37_n$, $37_{n+1}$, etc. with which is associated the convolved value by which the weighting factor stored in the same memory location must be multiplied. In most memory locations of the weighting factor matrix two weighting factors and two measurement path numbers are stored. For some elements $\epsilon_1$ only one weighting factor and one measurement path number will be required for calculating the attenuation contribution (as will be apparent from the Figure).

It can be readily seen that, if all convolved values associated with the source position $\theta_1$ have been processed, the convolved values associated with the source position $\theta_2$ can be processed, after the matrix in which the weighting factors and measurement path numbers are stored has been rotated through an angle $\Delta\theta(=\Delta\phi!)$ with respect to the matrix of elements (in the direction of rotation of the source 1!). The configuration of the two matrices will not have changed, with respect to the source 1 except for the angular coordinate of the matrix of elements. The matrix containing the weighting factors and the measurement path numbers, however, will remain the same, so that each weighting factor and associated measurement path number can be used without modification. This enables the weighting factor to be calculated in advance and stored with the measurement path number in a memory (e.g. a R.O.M.). It can also be seen that the matrix will be symmetrical with respect to the connecting line between the source 1 and the centre 9, so that it is sufficient to store the weighting factors and associated measurement path numbers relating to only half the matrix.

As will be apparent from FIG. 2, the elements $\epsilon$ are not all of the same size. In order to obtain a substantially uniform information density, the attenuation values determined in respect of neighbouring elements $\epsilon$ (for example, between two concentric circles 31) are summed to form an image element; the sum of the areas of the individual elements $\epsilon$ forming an image element should then approximate to a "standard unit of area". If the central element 40 has a radius r (element 40 need not be subdivided, because it remains in position regardless of the rotation of the matrix), the area will be $\pi r^2$ and this is used to define the standard unit of area. The area of an element $\epsilon$ between the concentric circles 31 having a radius n·r and (n-1)·r will be equal $$(\pi/M)\cdot\{(n\cdot r)^2-(n-1)^2\cdot r^2\}$$

in which M is the number of elements defined by adjacent radial lines 33 between two circles 31. A number P times the area of this element will then most nearly equal $\pi\cdot r^2$, namely the standard unit of area, when P=M/2n (for which P should be an integer). If the number of source positions $\theta_i$ equals 360 (one group of measurement signals per degree of rotation), four attenuation values each associated with a corresponding image element occupying a standard unit of area will be produced in the second ring after summing over 90 elements defined by the radial lines 33. In the third ring, six attenuation values will be formed, each associated with a corresponding image element occupying a standard unit of area, after summing over each time 60 elements. In the fourth ring eight values will be formed each related to a corresponding image element, by summing over 45 elements, and so on. Each of the groups of measurement signals stored in the memory device 17 (see FIG. 1) is convolved in the processing device 16 with a known series of numbers, after which they are stored in the appropriate section 17a (FIG. 3) of the memory device 17 again. A clock 41 generates pulses which are applied, via a divide-by-four circuit 43, to a $\Delta\phi$-counter 45. The output of the counter 45 forms the first part of an address at which weighting factors and measurement path numbers are stored in a section 17b of the memory 17. Via a divide-by-M stage 47, the pulses are also applied to a ring number counter 49, the output of which forms a further part of the address at which the weighting factors and measurement path numbers are stored. In the addressed memory location in the memory 17b, at the most two weighting factors and four measurement path numbers will be stored. The weighting factors are identical for the coordinates (n, $\phi$) and (n, $-\phi$), but have to be multiplied by convolved values which are each associated with a different measurement path. The four measurement path numbers are applied in succession one at a time to the memory section 17a, via a connection 50 in response to successive clock pulses, for which purpose the memory section 17b is directly connected to the clock 41. In the memory section 17a there ae stored the convolved values associated with the measurement path numbers, and the convolved values are applied to a multiplier 51 one at a time. Furthermore, the weighting factors are applied simultaneously with the convolved values to the multiplier 51. The product of a weighting factor and a convolved value is applied to a summing device 53. The summing device 53 sums the products from the multiplier 51, for which purpose it receives pulses directly from the clock 41 for synchronizing the summing operations with the supply of the weighting factors and convolved value to the multiplier 51. Furthermore, the pulses from the clock 41 are applied to a divide-by-two circuit 55 which supplies, after each pair of clock pulses, a pulse to a section 17c of the memory. When a pulse is applied to the memory section 17c, the contents of the summing device 53 are stored in the memory section 17c. The address at which the contents of the summing device 53 are stored, is formed by the outputs of the $\Delta\phi$-counter 45 and the ring number counter 49, the contents being stored at the address (n, $\phi$) in response to a first pulse from the divide-by-two circuit 55, and at the address (n−φ) in response to a second pulse from the divide-by-two circuit 55. The first term (n) of the address (n, φ) is determined by the count state of the ring number counter 49, and the second term is determined by the count state of the Δφ-counter 45. The purpose of the various divider-circuits (43, 47, 55) will now be apparent. It will also be apparent that during a count cycle firstly all the elements of the outermost ring $40_n$ (see FIG. 2) are scanned, after which a change over is made to the ring $40_{n-1}$ which is adjacent thereto at the inner periphery. For this reason, the count output is not taken from the normal Q outputs of the ring number counter 49, but from the complementary outputs $\bar{Q}$. As soon as $\bar{Q}$ reaches the value 1, the Δφ-counter 45 is blocked for some time (4.M/2 pulses), so that an attenuation contribution to the central image element region $40_o$ is calculated only once. There is also provided an increment counter 54 which is decremented by one step when the counter position Q=1 reached, so that the matrix of elements stored in the memory section 17c is rotated addresswise through an angular increment Δθ=Δφ with respect to the matrix containing weighting factors and measurement path numbers stored in the memory section 17b, so that the next group of convolved values, determined in a next source position, can be processed. The attenuation contributions stored in the memory section 17c have to be summed over various groups of elements in the different "rings 40" as hereinbefore explained before an attenuation distribution can be displayed with a uniform information density.

The part of a processing device 16 (of FIG. 1) which is shown in FIG. 4 is partly the same as the block diagram shown in FIG. 3. As will be apparent from FIG. 4, a contribution to the attenuation associated with a given element, is not applied directly to the memory section 17c. The sums formed by the summing device 53 are applied to a gate circuit 57 by means of which the contributions to the attenuation value associated with the elements, are separated into contributions to the elements (n, φ) and (n, −φ), and are applied to summing circuits $59_+$ and $59_-$, respectively. The summing circuits $59_+$ and $59_-$ sum the calculated attenuation contributions relating to a number of neighbouring elements in a ring ($40_n$, FIG. 2), so that a uniform information density can be obtained by making the number of summing oprations in the summing circuits $59_+$, $_-$ dependent on a ring number n which indicates the radius of the ring. The output of the ring number counter 49, therefore, is connected to a read only memory 61 (ROM) in which a table is stored which indicates how many elements ε (actually the contributions calculated for the elements ε) are to be summed in a given ring. Furthermore, a divide-by-four pulse-counter 63 is connected to the clock 41 in order to count the number of contributions which have been calculated after the start of a count period. As soon as the count state of the divide-by-four pulse-counter 63 corresponds to a number of elements determined by the count state of the ring number counter 49, a comparator 65 supplies a pulse which is applied to the inputs c of the summing circuits $59_+$ and $59_-$. The sums of all the attenuation contributions calculated thusfar and present at that instant, are separately stored in a section 17c of the memory 17. The addresses at which the sums are stored are determined both by the separate inputs (for +φ and −φ) in the memory section 17c and by the count state of an address counter 67 which counts the number of pulses supplied by the comparator 65.

The output of the comparator 65 is furthermore connected to a reset input of the divide-by-four pulse-counter 53, so that after the sum of a number of associated attenuation contributions has been determined, the counter 63 is reset to zero.

The complementary outputs $\bar{Q}$ of the ring number counter 49 are used as in FIG. 3. As soon as the outputs $\bar{Q}$ carry the value 1, the Δφ-counter 45 is blocked via a connection 70, so that the contribution to the central element $40_o$ (see FIG. 2) is calculated only once. The ring number counter 49 is set to a starting position representing the outer ring of the matrix by the pulses which are continuously generated by the clock 41. This situation is detected by a comparator 71 which applies an additional pulse to the Δφ-counter 45 via an OR-gate 73. As a result, the addresses activated by the Δφ-counter 45 in the memory section 17b are all incremented. The object thereof is to rotate the polar matrix containing weighting factors and measurement path numbers addresswise with respect to the matrix in the memory section 17c, so that a next group of convolved values, determined during a subsequent measurement after rotation of the X-ray source, can be backprojected.

In the case of backprojection as described with reference to FIG. 4, the matrix with the weighting factors and the measurement path numbers, is addresswise rotated in the same direction as the X-ray source. In the case described with reference to FIG. 3, the matrix of elements in which the groups of convolved values are backprojected, is addresswise rotated in the opposite direction with respect to the radiation source, the matrix with weighting factors and measurement path numbers and the measurement paths themselves (actually the X-ray source) being considered, for purposes of computation, to be stationary.

The attenuation values stored in the memory section 17c (after backprojection of all groups of convolved values) can be displayed by way of a monitor having a circular or spiral beam scan deflection. It will be apparent that a translation (required only once) of the polar organized memory section 17c to a cartesian organized memory can be effected, after which the attenuation distribution can be displayed by a conventional monitor.

What is claimed is:

1. In a device for determining a radiation attenuation distribution in a sectional plane of a body comprising:
    radiation source means for generating a flat, fan-shaped beam of radiation which is directed in the sectional plane and which penetrates and spans the body;
    detector means for detecting radiation from the source means which passes through the body and for supplying groups of measurement signals indicative thereof;
    a supporting frame which supports the radiation source means and the detector means;
    drive means for moving at least the radiation source means and the supporting frame to irradiate the body from a plurality of directions;
    wherein the detector means functions to supply a group of measurement signals for each of said directions, which groups represent radiation attenuation along each of a group of measurement paths which extend fan-wise from the radiation source means; and further including processing means which function to convolute a group of measurement signals with a series of numbers and to backproject the measurement signals thus convoluted to obtain the distribution of radiation attenuation values in the body;

and memory means, connected to the processing means, which function at least to store the measurement signals and the distribution of attenuation values;

the improvement wherein:

the memory means comprises a first memory for storing attenuation values and a second memory for storing weighting values for use during backprojection of the convolved values, the attenuation values and weighting values being stored, respectively, at locations in the first and second memories which correspond to locations in the sectional plane which are defined by polar coordinates; and wherein the processing means transmits a distance coordinate signal and an angle coordinate signal to the first and second memories which signals function to address locations therein.

2. The device of claim 1 wherein the second memory is a read-only-memory.

3. The device of claim 1 or 2 wherein the drive means rotate the radiation source means about an axis which is disposed perpendicular to the plane and further comprising means for moving the supporting frame parallel to the plane.

* * * * *